United States Patent
Gerlach et al.

(10) Patent No.: US 6,872,202 B2
(45) Date of Patent: Mar. 29, 2005

(54) LASER SLIT LAMP WITH LASER RADIATION SOURCE

(75) Inventors: Mario Gerlach, Eisenberg (DE); Martin Wiechmann, Jena (DE); Olaf Kittelmann, Kleinmachnow (DE); Diego Zimare, Jena (DE); Michael Kempe, Kunitz (DE); Dirk Muehlhoff, Kunitz (DE); Alexander Kalies, Frauenpriessnitz (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 10/043,463

(22) Filed: Jan. 10, 2002

(65) Prior Publication Data

US 2002/0133145 A1 Sep. 19, 2002

(30) Foreign Application Priority Data

Jan. 11, 2001 (DE) .......................................... 101 00 857

(51) Int. Cl.[7] .............................................. A61B 18/18
(52) U.S. Cl. ................................. 606/10; 606/4; 606/11
(58) Field of Search ............................. 606/4, 6, 10–11, 606/16–18; 607/88–95

(56) References Cited

U.S. PATENT DOCUMENTS

| | | | | |
|---|---|---|---|---|
| 4,974,230 A | * | 11/1990 | Hemmati ..................... | 372/41 |
| 5,048,026 A | * | 9/1991 | Shaw et al. ..................... | 372/6 |
| 5,084,886 A | * | 1/1992 | Martin ......................... | 372/36 |
| 5,488,443 A | * | 1/1996 | Ota et al. ..................... | 351/221 |
| 5,688,264 A | * | 11/1997 | Ren et al. ..................... | 606/15 |
| 5,889,805 A | * | 3/1999 | Botez et al. ................... | 372/45 |
| 5,921,981 A | | 7/1999 | Bahmanyar et al. | |
| 6,363,088 B1 | * | 3/2002 | Alphonse et al. ............... | 372/6 |
| 6,530,918 B1 | * | 3/2003 | Ueno et al. .................... | 606/10 |
| 6,585,722 B1 | * | 7/2003 | Abe ............................. | 606/4 |

* cited by examiner

Primary Examiner—Roy D. Gibson
(74) Attorney, Agent, or Firm—Reed Smith LLP

(57) ABSTRACT

A laser slit lamp comprising a slit lamp base, a slit lamp head and a slit lamp microscope. The laser slit lamp is connected with an applicator. It comprises a device for uniting radiation from at least two radiation sources collinearly and for directing the radiation of a treatment beam or working beam onto the location to be treated in or on the eye of a patient, a device for generating a target beam or marking beam for targeting and observing the location to be treated in or on the eye, and an adjusting device in the applicator for changing the intensity and diameter of the working beam spot used for treatment. The radiation sources are laser radiation sources arranged in the slit lamp head, in the slit lamp base or in the slit lamp microscope for generating the working beam, illumination beam and/or target beam. Devices for control, regulation and monitoring are likewise arranged in the interior of the slit lamp.

14 Claims, 3 Drawing Sheets

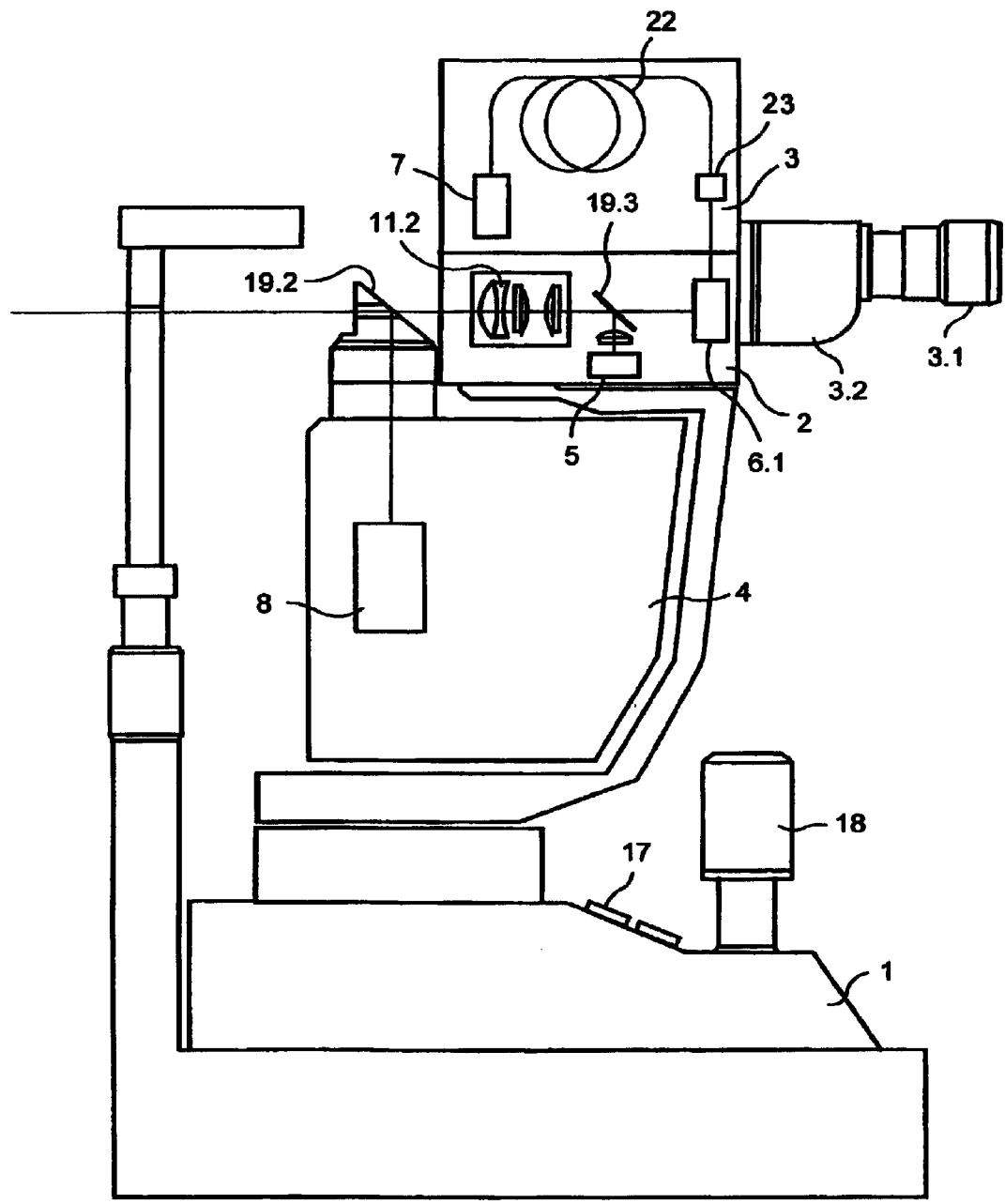
F I G. 3

LASER SLIT LAMP WITH LASER RADIATION SOURCE

CROSS-REFERENCE TO RELATED APPLICATIONS

This application claims priority of German application No. 101 00 857.0, filed Jan. 11, 2001, the complete disclosure of which is hereby incorporated by reference.

BACKGROUND OF THE INVENTION a) Field of the Invention

The invention is directed to a laser slit lamp with a laser radiation source and relates to the field of ophthalmology for diagnostic and therapeutic applications. Slit lamps with laser applicators are used in this field particularly for treatments of the retina such as panretinal photocoagulation in diabetic retinopathy, retinal welding in retinal detachment, grid coagulation of the retina in age-related macular degeneration (AMD) and for glaucoma treatments, e.g., trabeculoplasty in chronic glaucoma or iridotomy in acute glaucoma.

b) Description of the Related Art

Special laser slit lamps or diagnostic slit lamps with special link systems or applicators from many different manufacturers which are connected by a light-conducting fiber arrangement to an external (remote) laser radiation source generating a working beam and/or target beam are known in the art and are commercially available. Such laser slit lamps or link systems for diagnostic slit lamps are also described in the patent literature and other literature, for example, in U.S. Pat. No. 5,921,981. Combinations of a diode laser with a slit lamp or of an Nd:YAG laser with a slit lamp are known in this connection.

The usable wavelengths of laser radiation are in the near infrared and visible spectral region. Optical zoom systems are used in the optical outfitting of the applicator for adjusting the treatment spot sizes. Pulsed operation of the working radiation sources by means of intensity modulation of the pump source or by mechanical modulation (shutter mechanisms) is also known.

The extensive space requirement for the external laser source and the beam losses occurring on the path from the radiation source, via the slit lamp with the applicator, to the eye of the patent have proven to be substantial disadvantages in known combinations of external lasers and slit lamps. In order to overcome this disadvantage, it is necessary to compensate for the transfer losses by means of higher optical and electrical source powers. Other disadvantages include the high number of electric connection lines between the laser radiation source and the applying system, high setup costs, and light transfer via a sensitive light-conducting fiber to the applying system (laser slit lamp or link system).

It is the object of the invention to provide a laser slit lamp which extensively overcomes the disadvantages of the prior art and which provides a compact therapeutic and diagnostic device for medical laser applications in the field of ophthalmology.

According to the invention, this object is met in a laser slit lamp according to the preamble of the first patent claim by the characterizing means shown in this claim. Details and other constructions of the invention are described in the subclaims. The installation of a very compact diode-supported laser radiation source, including supply and control arrangements, in a slit lamp is particularly advantageous. A continuous and/or pulsed diode-pumped solid state laser, a fiber laser, a microchip laser or a diode laser, for example, can be used as the laser radiation source. The use of semiconductor laser diodes as a marking source, pumping source or treatment source ensures low electrical and optical losses. The device therefore operates very efficaciously with high efficiency. Because of this, special measures for cooling and heat dissipation can be dispensed with.

Accordingly, it is advantageous when the internal laser radiation source is a compact diode-pumped frequency-doubled solid state laser which is arranged, together with the pump light source and a nonlinear doubler crystal, in the slip lamp head, in the applicator or in the slit lamp microscope, the nonlinear crystal being arranged inside or outside the laser cavity.

It is also advantageous when Nd:YAG crystals, Nd:YVO$^4$ crystals or Nd:YLF crystals are provided as laser materials for the laser radiation source and the light emission is carried out on the fundamental wavelength at 1064 nm, 1053 nm or 1047 nm. The frequency-doubled working radiation source emits at a wavelength of 532 nm, 562.5 nm or 523.5 nm with output powers of up to about 3 W. The wavelength of the pump radiation is in the range of 790 nm to 815 nm.

In an advantageous arrangement, the laser crystal can be connected in a known manner with the pump radiation source by a passive optical coupling element. This coupling element can be realized, for example, by means of a light guide with imaging optics.

According to another embodiment form, an up-conversion fiber laser is provided as internal laser radiation source, its active fiber laser core is Pr/Yb-doped and the emission wavelength of the working beam is 520 nm to 540 nm or 630 nm to 640 nm with output powers of up to 2.5 W. The pump radiation source can be arranged in the slit lamp base and the wavelength of the pump radiation is preferably in the range of 830 nm to 850 nm. In this case, the pump radiation source is advantageously connected with the fiber by coupling optics for coupling the pump radiation output into the active fiber core.

Another favorable arrangement results when an up-conversion fiber laser whose active fiber core is erbium-doped and whose laser emission has an output power of up to 2.5 W is provided as an internal laser radiation source. The wavelength of the laser radiation is 547 nm. The wavelength of the pump radiation is in the range of 970 nm to 980 nm and the pump radiation source is connected with the fiber by coupling optics for coupling the pump radiation output into the active fiber core.

It is also advantageous when the internal laser radiation source is an externally frequency-doubled fiber laser whose fiber core is neodymium-doped, wherein the fundamental wavelength is in the range of 1060 nm to 1080 nm and the wavelength of the working beam at output powers of up to about 2.5 W is in the range of 530 nm to 540 mm, and when poled or unpoled nonlinear optical crystals are provided for doubling, the wavelength of the pump radiation is in the range of 800 nm to 820 nm and the pump radiation source is provided with coupling optics which make possible an effective coupling of the pump radiation into the active fiber core.

An intracavity frequency-doubled fiber laser with a neodymium-doped fiber laser core can also be provided as an internal laser radiation source and a nonlinear optical crystal can be provided for frequency doubling, wherein the fundamental wavelength is in the range of 1060 nm to 1080 nm and the frequency-doubled emission wavelength of the working beam at an output power of up to 2.5 W is 530 nm to 540 nm.

Further, is it advantageous when a radiation source generating the target beam or marking beam is arranged in the slit lamp head or in the slit lamp microscope.

The pump radiation source can advantageously be a diode laser which is arranged in the slit lamp base or in the slit lamp head and whose pump radiation has a wavelength in the range of 800 nm to 820 nm, the pump diode being provided with coupling optics for effective coupling of the pump radiation into the active fiber core.

The target beam or marking beam is coupled collinearly into the working beam in a simple manner by a dichroic mirror or by polarizing elements.

Further, it is advantageous that at least one light-conducting fiber connection is provided at the slit lamp base, at the slit lamp head or at the slit lamp microscope for connecting external applicators, for example, endoprobes or head ophthalmoscopes.

A compact therapeutic laser instrument is realized by the laser slit lamp according to the invention. In particular, optical coupling losses are also reduced by the arrangement of internal radiation sources. Further, expenditure on cables is reduced considerably. A very low setup cost and small space requirement are achieved by eliminating optical transfer between a radiation source which is arranged remote from the slit lamp and the applying slit lamp. It is also possible to connect alternative applicators.

There are three basic possibilities for the arrangement of the laser radiation source, namely, the arrangement of the laser source in the slit lamp head, in the slit lamp microscope or in the slit lamp base.

The pump source can be located directly at the working beam source or in another part of the laser slit lamp. Electronics for control, regulation, monitoring and supply are advantageously located in the base of the laser slit lamp. The power supply part of the laser slit lamp can be arranged in the slit lamp base as well as externally. Higher transport voltages are advantageously used in order to ensure the transport of the electric power through highly flexible lines with a small cross section. A voltage-current conversion is then carried out in the immediate vicinity of the electric consumers (laser diodes, thermoelectric coolers, etc.).

Accordingly, the invention has the following advantages:

a compact therapeutic laser instrument is achieved;

optical coupling losses are reduced, i.e., greater efficiency, reduced initial costs and operating costs as a result of lower system powers;

low-maintenance due to compact closed assembles;

external radiation source with extensive cable is eliminated;

optical transfer between the radiation source and the applying slit lamp is eliminated;

very low setup costs and small space requirement;

possibility of connecting other alternative applicators to the laser slit lamp.

The invention will be described more fully in the following with reference to an embodiment example.

BRIEF DESCRIPTION OF THE DRAWINGS

In the drawings:

FIG. 3 shows a laser slit lamp with radiation sources in the applicator and slit lamp head.

DESCRIPTION OF THE PREFERRED EMBODIMENTS

Figure 1:
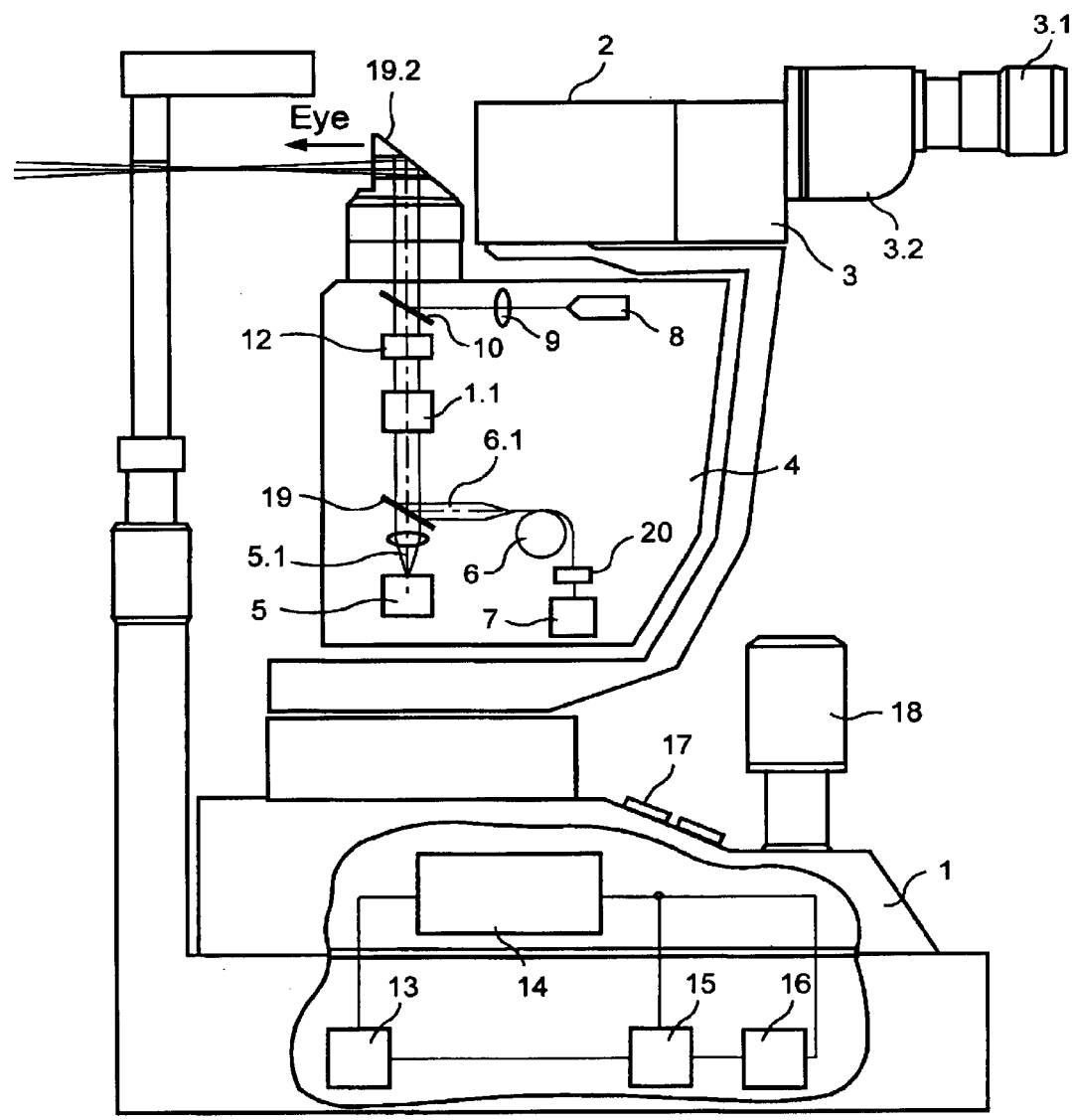
FIG. 1 shows a laser slit lamp with applicator and arrangements for controlling, regulating and monitoring.

The laser slit lamp according to the invention which is shown in a simplified manner in FIG. 1 comprises a slit lamp base 1, a slit lamp head 2 and a slit lamp microscope 3 with eyepiece 3.1 and tube 3.2 for observing the eye to be treated and the area or point in or on the eye to be treated. An applicator 4 having means for uniting radiation from different radiation sources collinearly is connected to the slit lamp. These radiation sources can be marking or target radiation sources 5 which supply a target beam or marking beam 5.1 or a working radiation source 6 which generates a treatment beam or working beam 6.1 and which is shown in FIG. 1 as a fiber laser. A radiation source 7 generating the pump radiation is arranged in the applicator 4 in this arrangement for generating the laser radiation source used for operation as working radiation source 6. In the slit lamp according to FIG. 4, all other radiation sources are also arranged in the applicator 4.

An illumination radiation source 8 is provided in the applicator 4 for illuminating and observing the area to be treated, its radiation being directed into the eye by imaging and/or deflecting optical elements 9; 10.

In order to change the spot size of the working beam 6.1 and/or target beam 5.1, zoom optics 11 are advantageously provided in the beam path in the applicator 4. Additional optical components 12 serve to image and focus the beam in the beam path in which they are arranged. The target beam 5.1 is advantageously coupled into the working beam 6.1 collinearly in the arrangement according to FIG. 1 by a dichroic mirror 19. It is accordingly ensured during treatment of the eye that the target beam 5.1 and working beam 6.1 impinge on the same location in or on the eye.

Controlling, regulating and monitoring arrangements necessary for operation and for control of the laser slit lamp are provided in the interior of the laser slit lamp, preferably in the slit lamp base 1. Thus, for example, the power supply part 13, a safety and regulating logic 14, a computer unit 15 and diode driver, including Peltier elements 16 for temperature regulation and corresponding connections, are arranged in the slit lamp base 1. Operating controls 17 and operating levers 18 are likewise arranged in the slit lamp base 1. They are provided for operating and adjusting the slit lamp.

FIG. 1 shows a laser slit lamp in which the working radiation source 6 which is arranged internally is, for example, a diode-pumped, up-conversion fiber laser which is arranged in the applicator 4 and which is operated in continuous or pulsed mode. The fiber core of this fiber laser is Pr/Yb-doped and the fiber laser emits a working beam with a wavelength in the range of 520 nm to 540 nm or in the range of 630 nm to 640 nm, with an output power of up to 2.5 W.

Alternatively, in Pr/Yb fiber lasers, a fluorescent line in the radiation spectrum of the laser which is sufficiently remote from the wavelength of the working beam can be used as a target beam.

In this construction, the pump radiation source 7 is likewise arranged in the applicator 4 and emits pump radiation in the wavelength range of 830 nm to 850 nm which is coupled into the active fiber core of the fiber laser in a manner known per se. Transfer or coupling optics 20 can be provided between the pump radiation source 7 and the working radiation source 6 (fiber laser) for coupling in.

In the construction according to FIG. 1, an up-conversion fiber laser whose fiber core is erbium-doped and whose working beam has an output power of up to 2.5 W can also be provided as an internal working radiation source 6. The wavelength of the laser beam is then at 547 nm. The pump radiation for optical excitation of the fiber laser is in the range of 970 nm to 980 nm.

A frequency-doubled fiber laser with a neodymium-doped or ytterbium-doped fiber core can also be used as an internal working radiation source 6, wherein the fundamental wavelength of the emitted laser beam is 1060 nm to 1100 nm. The wavelength of the frequency-doubled working beam is then 530 nm to 550 nm. The output power is again up to 2.5 W. The doubling of the frequency of the laser radiation generated by the fiber laser can be realized in a manner known per se by extracavity and intracavity nonlinear optical crystals, i.e., the doubler crystals are arranged inside or outside the respective laser cavity. The pump radiation source 7 transmits a pump radiation with a wavelength in the range of 800 nm to 820 nm and is provided with coupling optics 20 which allow an efficient incoupling of the pump radiation into the active fiber core of the fiber laser.

Figure 2:
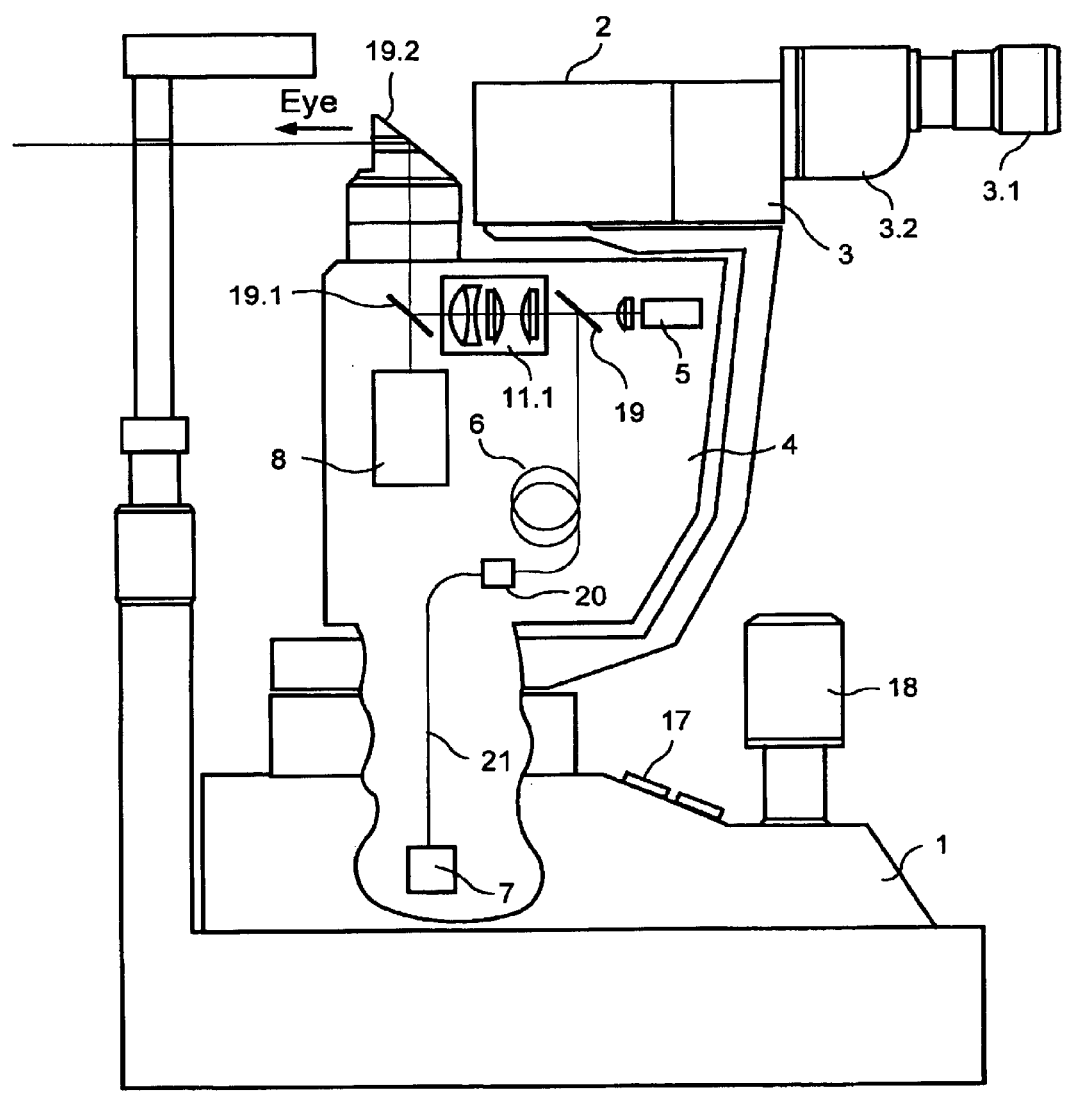
FIG. 2 shows a laser slit lamp with an applicator with radiation sources in the applicator and in the slit lamp base.

Like the laser slit lamp according to FIG. 1, the laser slit lamp shown in FIG. 2 comprises a slit lamp microscope 3 with eyepiece 3.1, tube 3.2, an applicator 4 and the slit lamp base 1 with operating controls 17 and operating levers 18. In FIG. 2, as also in the other Figures, parts and component groups having the same function are substantially designated by the same reference numbers.

The pump radiation source 7, for example, a corresponding laser diode, is arranged in the slit lamp basis 1. The pump radiation is directed to coupling optics 20 in the applicator 4 via a light guide 21 and is coupled into the working radiation source 6 which is constructed as a fiber laser. The working beam emitted by the fiber laser is directed into the patient's eye by the dichroic mirror 10 through which the target beam emitted by the target radiation source 6 is coupled into the working beam collinearly, as well as through the zoom optics 11.1 and mirrors 19.1 and 19.2. The illumination radiation emitted by the illumination radiation source 8 can also be coupled into the working beam by the dichroic mirror 19.1.

The laser slit lamp according to the invention shown in FIG. 3 likewise comprises a slit lamp base 1, a slit lamp head 2, a slit lamp microscope 3 and an applicator 4. A working radiation source 6.1 is arranged in the slit lamp head 2 and is constructed, for example, as a microchip laser or as a suitable diode-pumped solid state laser. The solid state laser can be an intracavity or extracavity frequency-doubled laser in continuous or pulsed operation whose working beam is directed to the location to be treated in or on the patient's eye through a dichroic mirror 19.3 by zoom optics 11.2. The target radiation source 5 is likewise arranged in the slit lamp head 2, its target beam being coupled into the beam path of the working beam collinearly through the mirror 19.3. The pump radiation emitted by the pump radiation source 7, e.g., a pump diode, which is likewise arranged in the slit lamp head 2, is supplied for excitation through a light guide 22 through interposed coupling optics 23 of the working radiation source 6.1. In this embodiment example, the illumination radiation source 8 is located in the applicator 4 whose illumination beam is directed into the eye of the patient after being reflected at the mirror 19.2 (FIG. 3). Crystals or glasses doped with Nd, Er, Yb or $Cr^{3+}$ can be used as laser material in a manner known per se. Frequency doubling is also carried out in this case in a known manner by nonlinear optical crystals. For example, a frequency-doubled Nd-doped diode-pumped solid state laser emits radiation in a wavelength range of 530 nm to 550 nm and is excited by a pump radiation in a wavelength range of 790 nm to 820 nm.

The following is not shown in FIGS. 1 to 3:

Instead of arranging the pump radiation source 7 in the slit lamp head, as is shown in FIG. 3, the pump radiation source 7 can also be arranged in the slit lamp base 1. The pump radiation is then also supplied to the laser crystal through a corresponding light guide. The electric and electronic units needed for energy supply, control and regulation can also be accommodated in the slit lamp base in the construction according to FIG. 3.

For example, when a laser diode serving as pump source is arranged directly at the laser material, the transport of electrical energy is preferably and advantageously carried out by higher voltages and sharply reduced currents. An electric conversion to lower voltages and higher currents is then carried out directly in front of the diode. It is advantageous to carry out a redundant power measurement and monitoring before the working beam exits from the device.

While the foregoing description and drawings represent the present invention, it will be obvious to those skilled in the art that various changes may be made therein without departing from the true spirit and scope of the present invention.

What is claimed is:

1. A laser slit lamp comprising:
   a slit lamp base;
   a slit lamp head; and
   a slit lamp microscope;
   said laser slit lamp being connected with an applicator having means for uniting radiation from at least two radiation sources collinearly and for directing the radiation of a treatment beam or working beam onto the location to be treated in or on the eye of a patient;
   means for generating a marking beam or target beam for targeting and observing the location to be treated in or on the eye; and
   adjusting means in the applicator for changing the intensity and diameter of the working beam spot used for treatment;
   at least one radiation source being a laser radiation source arranged in the slit lamp head, in the slit lamp base or in the slit lamp microscope for generating the working beam, illumination beam and/or target beam; and
   devices for control, regulation and monitoring being arranged in the interior of the slit lamp.

2. The laser slit lamp according to claim 1, wherein the internal laser radiation source is a diode-pumped, frequency-doubled solid state laser which is arranged, together with the pump light source and a nonlinear doubler crystal, in the slip lamp base, in the slit lamp head or in the slit lamp microscope, the nonlinear crystal being arranged inside or outside the laser cavity.

3. The laser slit lamp according to claim 1, wherein an Nd:YAG crystal, Nd:YVO$^4$ crystal or Nd:YLF crystal is provided as laser material for the laser radiation source and the radiation has a fundamental wavelength of 1064 nm, 1047 nm or 1053 nm, and the wavelength of the pump radiation generated by the pump radiation source is in the range of 790 nm to 811 nm, and wherein the frequency-doubled working beam emitted on the wavelength of 532 nm, 523.5 nm or 562.5 nm has an output power of up to about 3 W.

4. The laser slit lamp according to claim 1, wherein the laser crystal is connected in a manner known per se with the pump radiation source by a passive optical coupling element.

5. The laser slit lamp according to claim 1, wherein an up-conversion fiber laser is provided as internal laser radiation source, its active fiber laser core is Pr/Yb-doped, wherein the emission wavelength of the working beam is 520 nm to 540 nm or 630 nm to 640 nm with output powers of up to 2.5 W, wherein the pump radiation source is arranged in the slit lamp base and the wavelength of the pump radiation is in the range of 830 nm to 850 nm, and wherein the pump radiation source is connected with the fiber by coupling optics for coupling the pump radiation output into the active fiber core.

6. The laser slit lamp according to claim 1, wherein an up-conversion fiber laser whose active fiber core is erbium-doped and whose working beam has an output power of up to 2.5 W is provided as an internal laser radiation source, wherein the wavelength of the pump radiation is in the range of 970 nm to 980 nm, and wherein the pump radiation source is connected with the fiber by coupling optics for coupling the pump radiation output into the active fiber core.

7. The laser slit lamp according to claim 1, wherein the internal laser radiation source is a frequency-doubled fiber laser whose fiber core is neodymium-doped or ytterbium-doped, in that the fundamental wavelength ranges from 1060 nm to 1100 nm and the wavelength of the working beam at output powers of up to about 2.5 W is in the range of 530 nm to 550 nm, wherein poled or unpoled nonlinear optical crystals are provided outside the cavity for doubling, and wherein the wavelength of the pump radiation is in the range of 800 nm to 820 nm and the pump radiation source is provided with coupling optics which make possible an effective coupling of the pump radiation into the active fiber core.

8. The laser slit lamp according to claim 1, wherein the internal laser radiation source is an intracavity frequency-doubled fiber laser with a neodymium-doped or ytterbium-doped fiber laser core and a nonlinear optical crystal is provided for frequency doubling, wherein the fundamental wavelength is in the range of 1060 nm to 1100 nm and the emission wavelength of the working beam at an output power of up to 2.5 W is 530 nm to 550 nm.

9. The laser slit lamp according to claim 1, wherein a radiation source generating the target beam or marking beam is arranged in the slit lamp base or in the slit lamp microscope.

10. The laser slit lamp according to claim 1, wherein the pump radiation source is a diode laser which is arranged in the slit lamp base and has a pump wavelength in the range of 800 nm to 820 nm, the pump diode being provided with coupling optics for effective coupling of the pump radiation into an active fiber core.

11. The laser slit lamp according to claim 1, wherein the target beam or marking beam is coupled collinearly into the working beam by a dichroic mirror or by polarizing elements.

12. The laser slit lamp according to claim 1, wherein the target beam or marking beam is formed by fluorescent radiation of an up-conversion fiber laser which is at a spectral distance from the working radiation.

13. The laser slit lamp according to claim 1, wherein at least one light-conducting fiber connection is provided at the slit lamp base or at the slit lamp microscope for connecting external light-conducting fibers of endo-applicators.

14. A laser slit lamp device comprising:
   a laser slit lamp including:
      a slit lamp base;
      a slit lamp head coupled to the slit lamp base; and
      a slit lamp microscope coupled to the slit lamp head;
      the laser slit lamp being coupled to an applicator that is operable to collinearly unite and direct a targeting beam and a treatment beam onto the eye of a patient;
   a first beam source operable to generate the targeting beam to target and observe the location to be treated in or on the eye;
   a second beam source operable to generate the treatment beam;
   a beam adjuster operable to adjust the intensity and diameter of the treatment beam;
   wherein at least one of the first and second beam sources is a laser radiation source that is arranged in the laser slit lamp, and the beam adjuster is arranged in the interior of the laser slit lamp.

* * * * *